United States Patent
Ogawa

(10) Patent No.: US 9,877,704 B2
(45) Date of Patent: Jan. 30, 2018

(54) PHANTOM USED FOR ACOUSTIC DIAGNOSTIC APPARATUS

(71) Applicant: CANON KABUSHIKI KAISHA, Tokyo (JP)

(72) Inventor: Ryo Ogawa, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 55 days.

(21) Appl. No.: 15/039,378

(22) PCT Filed: Nov. 20, 2014

(86) PCT No.: PCT/JP2014/081485
§ 371 (c)(1),
(2) Date: May 25, 2016

(87) PCT Pub. No.: WO2015/080236
PCT Pub. Date: Jun. 4, 2015

(65) Prior Publication Data
US 2017/0020491 A1   Jan. 26, 2017

(30) Foreign Application Priority Data
Nov. 29, 2013 (JP) .................................. 2013-247129

(51) Int. Cl.
*A61B 8/00* (2006.01)
*A61B 5/00* (2006.01)

(52) U.S. Cl.
CPC ............ *A61B 8/587* (2013.01); *A61B 5/0095* (2013.01)

(58) Field of Classification Search
CPC .............................. A61B 8/587; A61B 5/0095
USPC ...................................... 73/1.82, 1.86, 866.4
See application file for complete search history.

(56) References Cited

FOREIGN PATENT DOCUMENTS

| EP | 1955655 A1 | 8/2008 |
|----|------------|--------|
| JP | H01-300935 A | 12/1989 |
| JP | 2007143946 A | 6/2007 |
| JP | 2011-209691 A | 10/2011 |
| WO | 2011/111572 A1 | 9/2011 |

OTHER PUBLICATIONS

Kazuhiro Yasukawa, An Ultrasound Phantom with Long-Term Stability Using a New Biomimic Soft Gel Material, 2007 IEEE Ultrasonics Symposium, 2501-2502.
Toshio Kondo, New Tissue Mimicking Materials for Ultrasound Phantoms, 2005 IEEE Ultrasonics Symposium, 1664-1667.

*Primary Examiner* — Robert R Raevis
(74) *Attorney, Agent, or Firm* — Canon U.S.A., Inc. IP Division

(57) ABSTRACT

An acoustic phantom of an embodiment is mainly made of a urethane gel produced by a reaction of a polyether polyol and an isocyanate compound. The urethane gel has a cross-linking index (CI) in the range of 1600 to 5000.

6 Claims, 3 Drawing Sheets

PHANTOM USED FOR ACOUSTIC DIAGNOSTIC APPARATUS

TECHNICAL FIELD

The present invention relates to a humanoid phantom used for quality control and calibration of acoustic diagnostic apparatuses.

BACKGROUND ART

Ultrasonic diagnostic apparatuses are used for medical diagnosis. These apparatuses monitor living bodies in vivo for diagnosis, using ultrasonic echo images formed by reflection in the living body. In addition, photoacoustic apparatuses using light have recently been developed for diagnosis. Photoacoustic apparatuses are intended for medical diagnosis. Such an apparatus irradiates a test area of a living body with light so that the measuring target is thermally expanded to generate acoustic waves (typically ultrasonic waves), and displays an image according to the signal of the acoustic waves. Such an acoustic diagnostic apparatus can measure specific substances at the test area, such as glucose and hemoglobin in the blood.

The quality control of such diagnostic apparatuses used for medical purposes is necessary for accurate diagnosis. Phantoms are used as reference materials for quality control and calibration of the diagnostic apparatuses.

Phantoms are required to propagate ultrasonic waves generated from a target that is a mimic tumor therein (or waves reflected from the target or the interface). In order to ensure highly accurate quality control and calibration of diagnostic apparatuses, the entirety of a phantom must have acoustic properties similar to the living body.

As phantoms used for quality control, urethane gels are generally used. Urethane gels are stable in physical properties with time and have acoustic properties close t to those of the living body. For example, PTL 1 discloses a urethane gel having optical and acoustic properties controlled for use as photoacoustic phantoms, produced by curing a copolymer of ethylene oxide and propylene oxide with an isocyanate. PTL 2 teaches that a urethane gel produced from polybutadiene polyol and diphenylmethane diisocyanate has acoustic properties suitable for use as ultrasonic phantoms.

CITATION LIST

Patent Literature

PTL 1 Japanese Patent Laid-Open No. 2011-209691
PTL 2 Japanese Patent No. 3650096

SUMMARY OF INVENTION

Technical Problem

A phantom suitable for acoustic diagnostic apparatuses satisfies the following requirements at the same time. One of the requirements is to have an acoustic attenuation coefficient approximated to that of the human body. The other is that the urethane gel is not so deformed as the target or signal source is displaced when the phantom is pressed for signal detection for measurement, or when an ultrasonic probe is pressed on the phantom for measurement.

Phantoms mainly containing the urethane gel disclosed in PTL 1 or 2 however do not satisfy these requirements at the same time.

Solution to Problem

An acoustic phantom of an embodiment of the invention mainly contains a urethane gel produced by a reaction of polyether polyol and an isocyanate and having a cross-linking index (CI) in the range of 1600 to 5000.

The cross-linking index (CI) is defined by the following equation (1):

[Math. 1]

$$CI = \frac{W_{OH}/C_{OH}}{([NCO]/[OH]) \cdot [([OH]/C_{OH}) - 1]} \quad (1)$$
$$C_{OH} = W_{OH}/M_{OH}$$
$$[OH] = W_{OH}/Eq_{OH}$$
$$[NCO] = W_0/Eq_0$$

where $W_U$: total weight of urethane gel (g);
$W_0$: weight (g) of isocyanate in $W_U$ (g) of urethane gel;
$W_{OH}$: weight (g) of polyether polyol in $W_U$ (g) of urethane gel;
$M_{OH}$: number-average molecular weight (g/mol) of polyether polyol;
$Eq_{OH}$: active hydroxy group equivalent weight (g/eq) of polyether polyol;
$Eq_0$: active isocyanate group equivalent weight (g/eq) of isocyanate compound;
$C_{OH}$: total moles of polyether polyol in $W_U$ (g) of urethane gel;
[OH]: moles of active hydroxy group in $W_U$ (g) of urethane gel; and
[NCO]: moles of active isocyanate group in $W_U$ (g) of urethane gel.

Further features of the present invention will become apparent from the following description of exemplary embodiments with reference to the attached drawings.

DESCRIPTION OF EMBODIMENT

Figure 1:
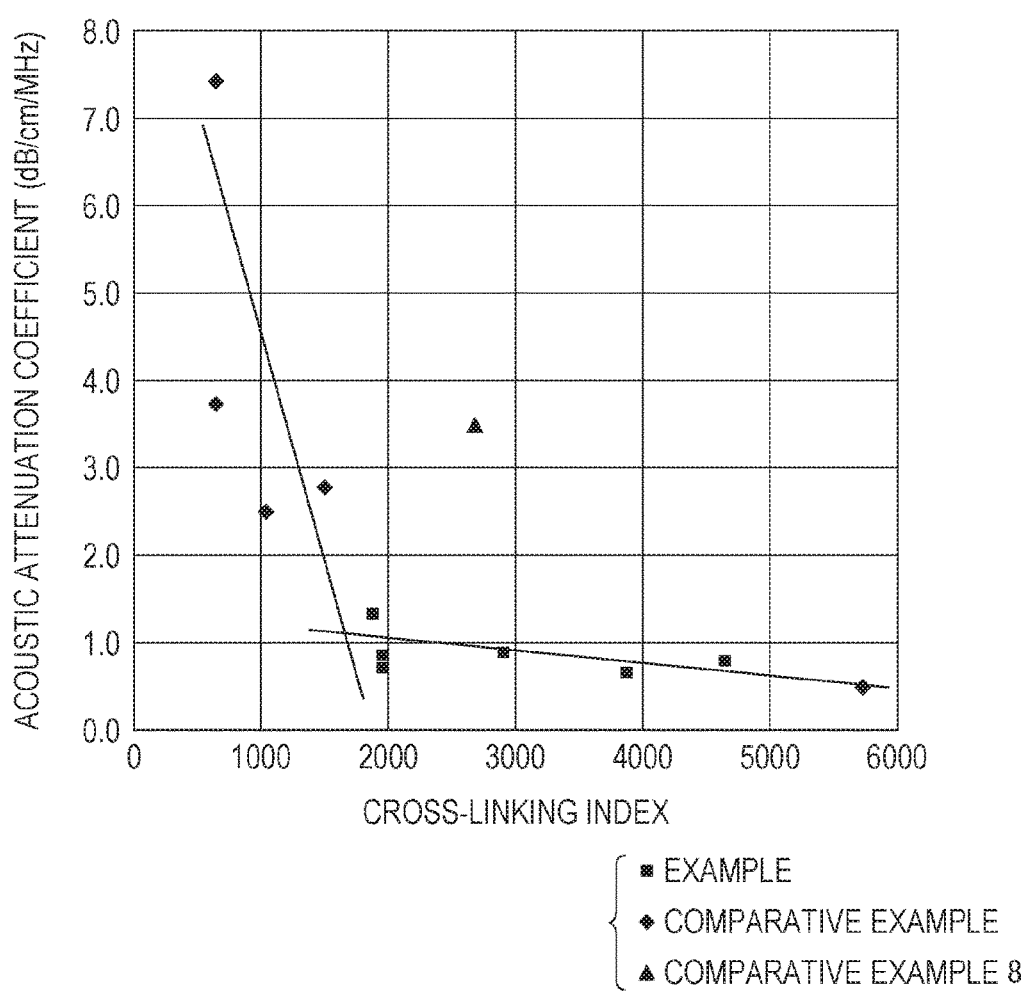
FIG. 1 is a plot showing the relationship between the cross-linking indices and acoustic attenuation coefficients of urethane gels.

An embodiment of the present invention will now be described. The embodiment disclosed herein describes ultrasonic and photoacoustic phantoms by way of example and is not intended to limit the invention.

Urethane Gel

Urethane gels, which are a type of thermosetting resin, are typically produced by a reaction between a polyol and an isocyanate.

The acoustic attenuation coefficient of soft tissue of the human body is typically in the range of 0.3 dB·cm$^{-1}$ to 2.0 dB·cm$^{-1}$. If the acoustic attenuation coefficient of a phantom lies outside this range, the attenuation of acoustic signals in the phantom differs from that of the living body, and accordingly quality control of diagnostic apparatuses becomes difficult.

The inventors found that urethane gels having cross-linking indices in the range of 1600 to 5000 can have acoustic attenuation coefficients close to those of human tissues (skin, fat, etc.).

The cross-linking index (CI) is defined by the following equation:

[Math. 2]

$$CI = \frac{W_{OH}/C_{OH}}{([NCO]/[OH]) \cdot [([OH]/C_{OH}) - 1]} \quad (1)$$

$$C_{OH} = W_{OH}/M_{OH}$$
$$[OH] = W_{OH}/Eq_{OH}$$
$$[NCO] = W_0/Eq_0$$

where $W_U$: total weight of urethane gel (g);

$W_0$: weight (g) of isocyanate in $W_U$ (g) of urethane gel;

$W_{OH}$: weight (g) of polyether polyol in $W_U$ (g) of urethane gel;

$M_{OH}$: number-average molecular weight (g/mol) of polyether polyol;

$E_{qOH}$: active hydroxy group equivalent weight (g/eq) of polyether polyol;

$E_{q0}$: active isocyanate group equivalent weight (g/eq) of isocyanate;

$C_{OH}$: total moles of polyether polyol in $W_U$ (g) of urethane gel;

[OH]: moles of active hydroxy group in $W_U$ (g) of urethane gel; and

[NCO]: moles of active isocyanate group in $W_U$ (g) of urethane gel.

Urethane gels, which are a type of thermosetting resin, are typically produced by a reaction between a polyol and an isocyanate.

Exemplary polyols include polyether polyol, polyester polyol, and polycarbonate polyol.

In order to produce a urethane gel having an acoustic attenuation coefficient close to that of the living body so as to be used for ultrasonic or acoustic phantoms, polyether polyol is used. Acoustic attenuation results mainly from energy loss during propagation of acoustic waves. The inventors found that acoustic waves can propagate in polyether polyol with small energy loss, and polyether polyol is therefore suitable.

Since the intermolecular interaction of polyether polyol is weak, polyether polyol molecules are expected to exhibit high mobility and allow ultrasonic waves to propagate without high energy loss, thus expected to be suitable for the present embodiment.

On the other hand, polyester polyols and polycarbonate polyols exhibit strong intermolecular interaction, and accordingly their molecules have low mobility. It is therefore estimated that these polyols do not allow sound waves to propagate without large energy loss, and accordingly have high acoustic attenuation coefficients. Polyester polyol and polycarbonate polyol can be therefore unsuitable for the phantom of the present embodiment having ultrasonic propagation properties similar to those of the living body.

The control of acoustic attenuation depends largely on the crosslink density of the urethane gel.

The crosslink density depends mainly on the molecular weight of the polyether polyol. In other words, by increasing the molecular weight of the polyether polyol, the density of cross-linking points formed by a reaction with isocyanate is reduced. Consequently, the molecules of the resulting urethane gel become easy to move and allow ultrasonic waves to propagate with low energy loss. Accordingly, the urethane gel exhibits a low acoustic attenuation coefficient.

If the amount of isocyanate added is small, at least one of the hydroxy groups of the polyether polyol molecule does not react. Thus, the number of polyether polyol chains capable of free movement increases and the number of cross-linking points capable of suppressing the movement of the molecular chains decreases. It is thus expected that the urethane gel exhibits enhanced mobility of the molecules thereof, low energy loss during propagation of ultrasonic waves, and a small acoustic attenuation coefficient.

Accordingly, the molecular structure and molecular weight of the polyol in the urethane gel and the amount of the isocyanate added are important in controlling acoustic attenuation.

The cross-linking index (CI) mentioned herein refers to an index representing the proportion in the urethane gel of the amounts of the polyether polyol component contributing to forming crosslinks and the polyether polyol component that does not react sufficiently. If the CI of a urethane gel has a high correlation with the mobility of the polyether polyol molecules in the urethane gel, the acoustic attenuation coefficient vary depending on the CI.

The present inventors have found that a urethane gel containing a polyether polyol designed so as to have a CI value of 1600 or more can achieve an acoustic attenuation coefficient of 2.0 dB·cm$^{-1}$ or less.

FIG. 1 shows that change in acoustic attenuation coefficient turns gentle at this CI value, and suggests that a phantom can have an acoustic attenuation coefficient close to that of the human body.

Figure 2:
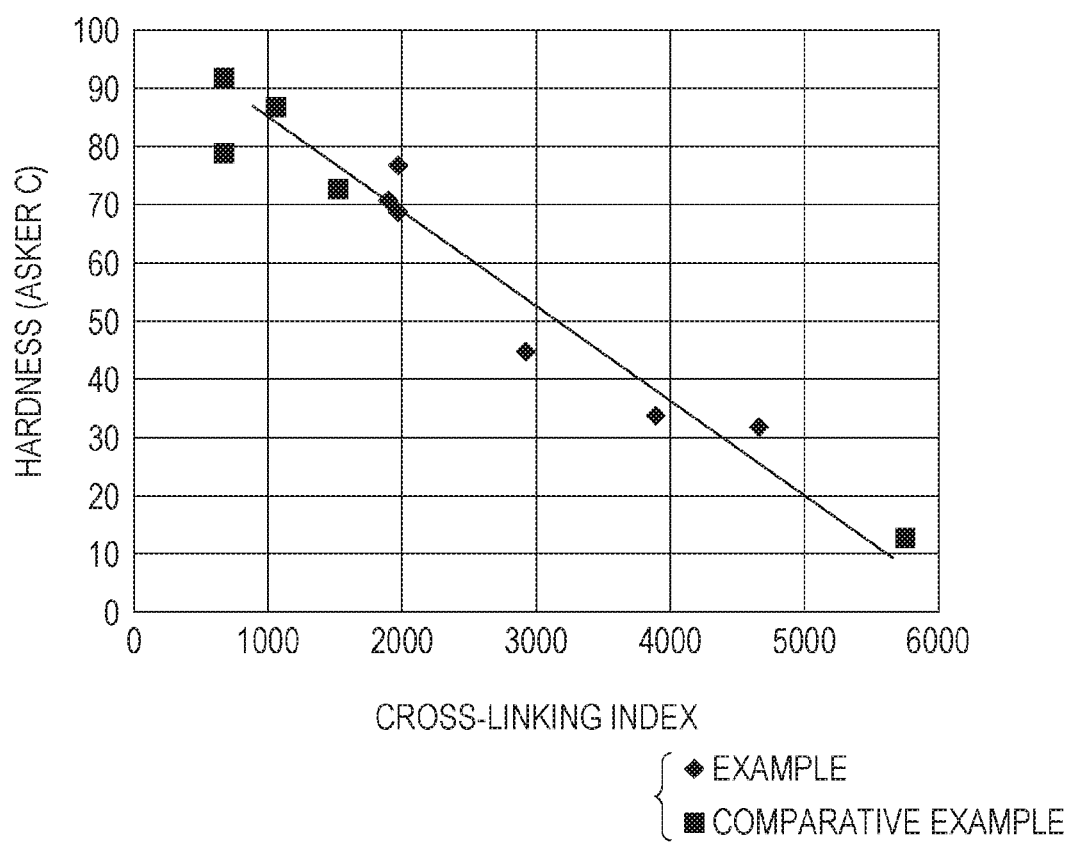
FIG. 2 is a plot showing the relationship between the cross-linking indices and hardnesses of urethane gels.

If a urethane gel having a CI larger than 5000, reaction cannot proceed sufficiently to produce urethane gel, or can produce a cured material having excessively low hardness. A soft phantom is unlikely to stand by itself, and causes the ultrasonic source or ultrasonic reflector disposed therein to be displaced. From the viewpoint of preventing this, the phantom desirably has an Asker C hardness of 20 or more. Phantoms having an Asker C hardness of 20 or more do not deform much and are suitable for use as phantoms for quality control. FIG. 2 suggests that the use of a urethane gel having a CI of 5000 or less can achieve a phantom having a favorable Asker C hardness.

A urethane gel having a cross-linking index (CI) in the range of 1600 to 5000 can be produced by appropriately controlling the amount of an isocyanate added to a polyether polyol selected from among the polyether polyols having different hydroxy group equivalent weights (moles of hydroxy group per gram) or different molecular weights.

The above described equation (1) is for a single-component urethane gel. For a urethane gel containing two or more polyether polyols, the physical property values of the urethane gels each can be estimated as an average property value of each polyether polyol. Hence, the CI of a urethane gel containing two or more polyether polyols can be calculated using the following equation (2), and the urethane gel of the present embodiment can be designed according to the CI calculated.

[Math. 3]

$$CI = \frac{W_{OH}/C_i}{([NCO]/[OH]) \cdot [([OH]/C_i) - 1]} \quad (2)$$

$$C_i = \sum_i (W_i/M_i)$$

$$[OH] = \sum_i (W_i/E_{q_i})$$

$$W_{OH} = \sum_i W_i$$

$$[NCO] = W_0/E_{q_0}$$

where $W_U$: total weight of urethane gel (g);
$W_i$: weight (g) of polyether polyol component i (i is 1 or more) in $W_U$ (g) of urethane gel;
$W_0$: weight (g) of isocyanate in $W_U$ (g) of urethane gel;
$W_{OH}$: total weight (g) of polyether polyols in $W_U$ (g) of urethane gel;
$M_i$: number-average molecular weight (g/mol) of polyether polyol component i;
$E_{qi}$: active hydroxy group equivalent weight (g/eq) of polyether polyol component i;
$E_{q0}$: active isocyanate group equivalent weight (g/eq) of isocyanate compound;
$C_i$: total moles of polyether polyols in $W_U$ (g) of urethane gel;
[OH]: total moles of hydroxy groups in $W_U$ (g) of urethane gel; and
[NCO]: total moles of isocyanate groups in $W_U$ (g) of urethane gel.

Polyether Polyol

The polyether polyol used in the present embodiment is not particularly limited as long as the molecule thereof has two or more hydroxy groups, and any polyether polyol may be used. The polyether polyol may be a single constituent or a combination of two or more polyether polyols. The polyether Polyol will be described below.

Polyether polyols that can be used in the present embodiment include ethylene glycol, 1,2-propanediol, 1,3-propanediol, 1,3-butanediol, 1,4-butanediol, neopentyl glycol, pentanediol, 1,6-hexanediol, 1,8-octanediol, 1,10-decanediol, 1-methyl-1,3-butylene glycol, 2-methyl-1,3-butylene glycol, 1-methyl-1,4-pentylene glycol, 2-methyl-1,4-pentylene glycol, 1,2-dimethyl-neopentyl glycol, 2,3-dimethyl-neopentyl glycol, 1-methyl-1,5-pentylene glycol, 2-methyl-1,5-pentylene glycol, 3-methyl-1,5-pentylene glycol, 1,2-dimethylbutylene glycol, 1,3-dimethylbutylene glycol, 2,3-dimethylbutylene glycol, 1,4-dimethylbutylene glycol, diethylene glycol, triethylene glycol, polyethylene glycol, dipropylene glycol, polypropylene glycol, 1,4-cyclohexanedimethanol, 1,4-cyclohexanediol, bisphenol A, bisphenol F, hydrogenated bisphenol A, and hydrogenated bisphenol F. These polyether polyols may be used singly or in the form of a polymer produced by polymerization of two or more thereof.

Preferably, the polyether polyol used in the present embodiment has a number-average molecular weight in the range of 500 to 7000 from the viewpoint of availability, and more preferably in the range of 1000 to 5000 from the viewpoint of low viscosity and easy handling. The number-average molecular weight can be measured by gel permeation chromatography (GPC).

The active hydroxy group equivalent weight of the polyether polyol can be determined by measuring the amount of hydroxyl groups by a known method. A method for determining the active hydroxy group equivalent weight from hydroxy value will now be described by way of example.

A polyether polyol is dissolved in pyridine containing acetic anhydride, and the hydroxy groups are thus acetylated. Then, the excess of the acetylating agent is hydrolyzed into acetic acid with water. The acetic acid is titrated with potassium hydroxide. An inflection point on the titration curve is defined as the end point. The hydroxy value of the polyether polyol is calculated from the amount of the potassium hydroxide solution used to reach the end point. The active hydroxy group equivalent weight can be derived from this hydroxy value.

Isocyanate

The urethane gel used in the present embodiment, which is a type of thermosetting resin, is produced by a reaction between a polyether polyol and an isocyanate. The isocyanate used in the present embodiment is not particularly limited as long as the molecule thereof has two or more isocyanate groups, and any isocyanate may be used. The isocyanate may be a single constituent or a combination of two or more isocyanates. The isocyanate will be further described, but is not limited to the compounds cited below.

Examples of the isocyanate that can be used in the present embodiment include aliphatic diisocyanates, such as tetramethylene diisocyanate, dodecamethylene diisocyanate, 1,4-butane diisocyanate, hexamethylene diisocyanate, 2,2,4-trimethylhexamethylene diisocyanate, 2,4,4-trimethylhexamethylene diisocyanate, lysine diisocyanate, 2-methylpentane-1,5-diisocyanate, and 3-methylpentane-1,5-diisocyanate; alicyclic diisocyanates, such as isophorone diisocyanate, hydrogenated xylylene diisocyanate, 4,4'-cyclohexylmethane diisocyanate, 1,4-cyclohexane diisocyanate, methylcyclohexylene diisocyanate, and 1,3-bis(isocyanate methyl)cyclohexane; aromatic diisocyanates, such as tolylene diisocyanate, 2,2'-diphenylmethane diisocyanate, 2,4'-diphenylmethane diisocyanate, 4,4'-diphenylmethane diisocyanate, 4,4'-diphenyldimethylmethane diisocyanate, 4,4'-dibenzyl diisocyanate, 1,5-naphthylene diisocyanate, and xylylene diisocyanate, 1,3-phenylene diisocyanate, 1,4-phenylene diisocyanate; and aromatic-aliphatic diisocyanates, such as dialkyldiphenylmethane diisocyanate, tetraalkyldiphenylmethane diisocyanate, and α,α,α,α-tetramethylxylylene diisocyanate. These isocyanates may be used singly or in combination.

The isocyanate may be used in a form modified to the extent that the intended effect of the embodiment can be produced. Examples of such a modified isocyanate include, but are not limited to, multimers (dimers such as uretdione-modified isocyanate, and trimers such as isocyanurate-modified isocyanate), biuret-modified isocyanates produced by, for example, a reaction with water, allophanate-modified isocyanates produced by, for example, a reaction with a monool or a low-molecular weight polyol, polyol-modified isocyanates produced by, for example, a reaction with a low-molecular weight polyol or a high-molecular-weight polyol, oxadiazinetrione-modified isocyanates produced by, for example, a reaction with carbon dioxide, and carbodiimide-modified isocyanates produced by, for example, decarbonate condensation.

The active isocyanate group equivalent weight of the isocyanate can be determined by measuring the amount of isocyanate groups by a known method. A method for determining the active isocyanate group equivalent weight will be described below by way of example.

An isocyanate is dissolved in a dehydrated toluene, and an excessive amount of di-n-butylamine solution is added to the solution of the isocyanate for a reaction. The unreacted di-n-butylamine is titrated with hydrochloric acid, and the inflection point on the titration curve is defined as the end point. The isocyanate group equivalent weight is calculated from the amount of the hydrochloric acid used to reach the end point.

Urethanation Catalyst

An appropriate amount of a catalyst may be added to the polyol or the isocyanate to accelerate the reaction between the hydroxy groups of the polyol and the isocyanate groups of the isocyanate. For example, a known urethanation catalyst may be added. Examples of such a catalyst include organic metal compounds, such as dibutyltin dilaurate, dibutyltin diacetate, and dioctyltin dilaurate; and organic amines and salts thereof, such as triethylenediamine and triethylamine. These catalysts may be used singly or in combination.

Optical Property-Adjusting Agent

For a phantom used for acoustic diagnostic apparatuses, in order to bring the light scattering and absorption properties of the phantom close to those of the human body, a light scattering material or a light absorbing material may be added to the urethane gel as an optical property-adjusting agent.

The light scattering material, which is a compound that can scatter light, is added to bring the light propagation property of the urethane gel close to that of human tissue, thereby controlling the equivalent scattering coefficient of the urethane gel.

The compound that can scatter light may be inorganic particles having a different refractive index from that of the urethane gel. Such inorganic particles may be made of any of silicon oxide, metal oxides, complex metal oxides, metal sulfides, metal compound semiconductors, metals, and diamond. Examples of metal oxides include aluminum oxide, titanium oxide, niobium oxide, tantalum oxide, zirconium oxide, zinc oxide, magnesium oxide, tellurium oxide, yttrium oxide, indium oxide, tin oxide, and indium tin oxide. Examples of complex metal oxides include lithium niobate, potassium niobate, and lithium tantalate. Examples of metal compound semiconductors include metal sulfides, such as zinc sulfide and cadmium sulfide, and zinc selenide, cadmium selenide, zinc telluride, and cadmium telluride. An example of metals is gold. Core-shell inorganic particles may be used which are particles of an inorganic compound coated with another inorganic material. The inorganic particles may have any shape, such as spherical, oval, depressed, or rod-like shape.

The inorganic particles used in the present embodiment can be selected from those exhibiting low absorption of wavelengths that acoustic diagnostic apparatuses use. In addition, the inorganic particles desirably have different refractive index from that of the urethane gel from the viewpoint of scattering light. The inorganic particles preferably have an average particle size in the range of 100 nm to 100 μm from the viewpoint of scattering light. In order to scatter light used for acoustic diagnosis effectively, the particle size of the inorganic particles are more preferably in the range of 200 nm to 10 μm. Examples of such inorganic particles include particles of inorganic oxides such as titanium oxide, and inorganic oxide particles having high refractive indices, such as zinc oxide and zirconium oxide, are advantageous.

The inorganic particles may be modified at the surfaces thereof. If particles of titanium oxide, which can be activated by light, are used, it is advantageous to modify the surfaces of the particles with an inorganic material, such as silica or alumina, to cover the surfaces. Alternatively, the surfaces of the inorganic particles may be modified with a dispersant containing an organic component so that the particles can be sufficiently dispersed in the urethane gel, which is an organic material. The dispersant containing an organic component may be selected those compatible with the urethane gel without particular limitation.

The light absorbing material can be selected from compounds that can absorb light having wavelengths used in acoustic diagnostic apparatuses without particular limitation as long as the intended effects of the embodiment are produced. Acoustic diagnostic apparatuses generally use light in a near-infrared region of 600 nm to 1100 nm, which can be easily transmitted through living bodies. It is therefore advantageous that the light absorbing material absorb light in this range.

Examples of the light absorbing material include the following known pigments. Blue pigments include phthalocyanine compounds and anthraquinone compounds. In addition to these compounds, metal-substituted or unsubstituted phthalocyanine compounds may be used. Red pigments include monoazo compounds, disazo compounds, azo lake compounds, benzimidazolone compounds, perylene compounds, diketopyrrolopyrrole compounds, condensed azo compounds, anthraquinone compounds, and quinacridone compounds. Green pigments include phthalocyanine compounds and anthraquinone compounds as with the case of blue pigments, and perylene compounds. Yellow pigments include monoazo compounds, disazo compounds, condensed azo compounds, benzimidazolone compounds, isoindolinone compounds, and anthraquinone compounds. Black pigments include Pigment Black 7 and carbon blacks. Furthermore, violet, orange, and brown pigments may be used as needed according to the light-absorbing property desired.

Other Additives

Any other additive, such as plasticizer, may be added to control the hardness or the acoustic properties of the urethane gel.

The plasticizer may be selected from known compounds. Known plasticizers include phthalic acid esters, trimellitic acid esters, pyromellitic acid esters, aliphatic monobasic acid esters, aliphatic dibasic acid esters, phosphoric acid esters, and polyhydric alcohol esters. These plasticizers may be used singly or in combination.

Phthalic acid esters include dimethyl phthalate, diethyl phthalate, dipropyl phthalate, diisopropyl phthalate, dibutyl phthalate, diisobutyl phthalate, diamyl phthalate, di-n-hexyl phthalate, dicyclohexyl phthalate, diheptyl phthalate, di-n-octyl phthalate, dinonyl phthalate, diisononyl phthalate, diisodecyl phthalate, diundecyl phthalate, ditridecyl phthalate, diphenyl phthalate, di(2-ethylhexyl) phthalate, di(2-butoxyethyl) phthalate, benzyl-2-ethylhexyl phthalate, benzyl-n-butyl phthalate, benzyl-isononyl phthalate, and dimethyl isophthalate.

Trimellitic acid esters include tributyl trimellitate, trihexyl trimellitate, tri-n-octyl trimellitate, tri-2-ethylhexyl trimellitate, and triisodecyl trimellitate.

Pyromellitic acid esters include tetrabutyl pyromellitate, tetrahexyl pyromellitate, tetra-n-octyl pyromellitate, tetra-2-ethylhexyl pyromellitate, and tetradecyl pyromellitate. Aliphatic monobasic acid esters include butyl oleate, methyl oleate, methyl octanoate, butyl octanoate, methyl dodecanoate, butyl dodecanoate, methyl palmitate, butyl palmitate, methyl stearate, butyl stearate, methyl linoleate, butyl linoleate, methyl isostearate, butyl isostearate, methylacetyl ricinoleate, and butylacetyl ricinoleate.

Aliphatic dibasic acid esters include dimethyl adipate, diethyl adipate, di-n-propyl adipate, diisopropyl adipate, diisobutyl adipate, di-n-octyl adipate, di(2-ethylhexyl) adipate, diisononyl adipate, diisodecyl adipate, di(2-butoxyethyl) adipate, di(butyl diglycol) adipate, heptylnonyl adipate, dimethyl azelate, di-n-octyl azelate, di(2-ethylhexyl) azelate, diethyl succinate, dimethyl sebacate, diethyl sebacate, dibutyl sebacic acid, di-n-octyl sebacic acid, di(2-ethylhexyl) sebacic acid, dibutyl fumarate, di(2-ethylhexyl) fumarate, dimethyl maleate, diethyl maleate, di-n-butyl maleate, and di(2-ethylhexyl) maleate.

Phosphoric acid esters include trimethyl phosphate, triethyl phosphate, tributyl phosphate, tri-n-amyl phosphate, triphenyl phosphate, tri-o-cresyl phosphate, trixylenyl phosphate, diphenyl-2-ethylhexyl phosphate, diphenyl cresyl phosphate, tris(2-butoxyethyl) phosphate, and tris(2-ethylhexyl) phosphate.

Polyhydric alcohol esters include diethylene glycol diacetylate, diethylene glycol dibenzoate, glycerol monooleate, glycerol tributyrate, glycerol triacetate, glyceryl tri(acetyl ricinoleate), and triethylene glycol diacetate.

Process for Producing Urethane Gel

The urethane gel of the present embodiment can be produced by thermal treatment of a curable composition mainly containing a polyether polyol and an isocyanate.

The curable composition mainly containing a polyether polyol and an isocyanate may further contain an appropriate amount of other additives, such as an optical property-adjusting agent, a urethanation catalyst, and a plasticizer.

The curable composition is poured into a mold and heat-treated. The heating temperature at this time is set according to the reactivity between the polyether polyol and the isocyanate, and may be set in the range of 40° C. to 200° C. For example, it may be set in the range of 60° C. to 120° C. from the viewpoint of reducing decomposition or coloring during heat treatment, and reducing remaining bubbles.

Ultrasonic Phantom

The urethane gel of the present embodiment may be used as an ultrasonic phantom by placing an ultrasonic reflector therein.

Figure 3:
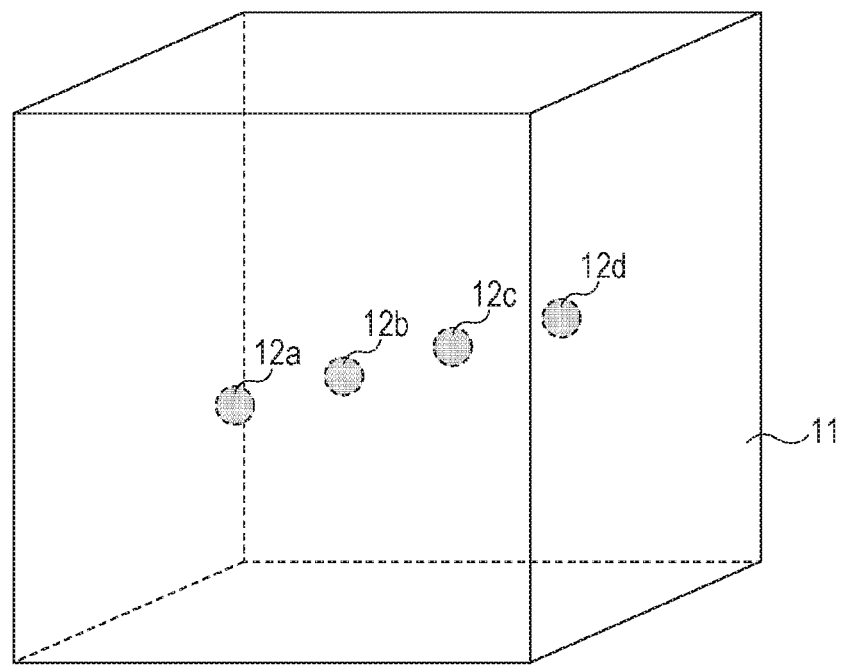
FIG. 3 is a schematic diagram of an ultrasonic phantom.

FIG. 3 shows the structure of a phantom according to an embodiment of the present invention, used for ultrasonic diagnostic apparatuses. Targets 12a to 12d that are mimic tumors are disposed in a urethane gel 11. This phantom measures 100 mm by 100 mm by 50 mm. The targets 12a to 12d in the phantom are spheres having a diameter of 5 mm and are disposed so that the centers thereof can be located at depths of 10 mm, 20 mm, 30 mm and 40 mm, respectively, when the phantom is set in an apparatus.

The targets 12a to 12d have a different acoustic impedance from that of the surrounding urethane gel, and may be made of a known material such as nylon or acrylic resin. Although the acoustic impedance of the targets 12a to 12d is desirably higher than the urethane gel and preferably 1.8 megarayls or more, it may be appropriately set to adjust the intensity of reflected waves to be measured.

The phantom is set in an ultrasonic diagnostic apparatus for measurement, and image contrast and the positions of the targets are measured with the diagnostic apparatus. The apparatus is thus calibrated with reference to the measurements.

Acoustic Phantom

The urethane gel of the present embodiment may be used as an acoustic phantom by placing therein an absorber that absorbs light to generate ultrasonic waves.

Figure 4:
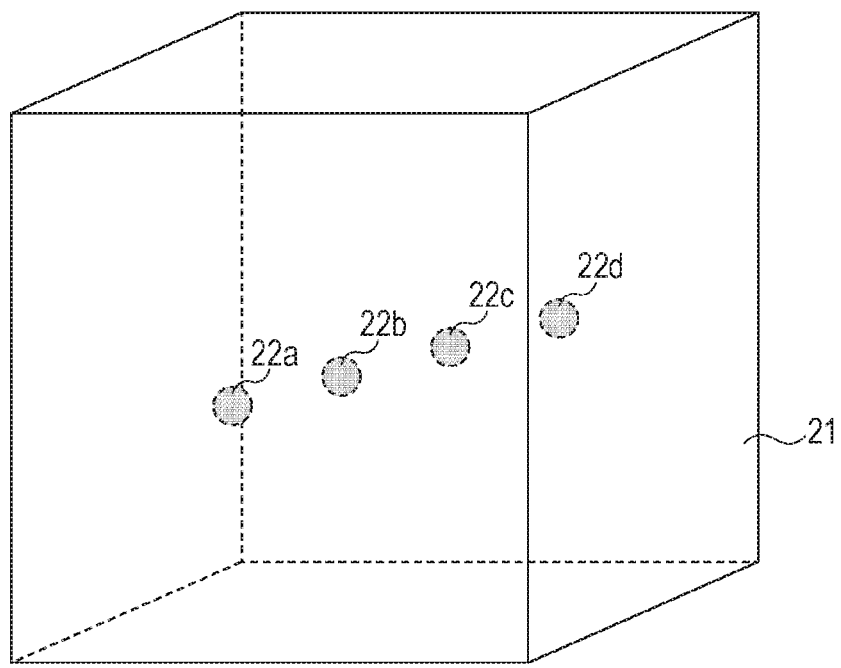
FIG. 4 is a schematic diagram of a photoacoustic phantom.

FIG. 4 shows the structure of a phantom according to an embodiment of the present invention, used for acoustic diagnostic apparatuses. Targets (absorbers that absorb light to generate ultrasonic waves) 22a to 22d that are mimic tumors are disposed in a urethane gel 21. This phantom measures 100 mm by 100 mm by 50 mm. The targets 22a to 22d in the phantom are spheres having a diameter of 5 mm and are disposed so that the centers thereof can be located at depths of 10 mm, 20 mm, 30 mm and 40 mm, respectively, when the phantom is set in an apparatus.

The targets 22a to 22d have the same absorption coefficient as actual tumors. For controlling the absorption coefficient of the targets, a known pigment may be added as in the case of the foregoing urethane gel.

The phantom is set in an acoustic diagnostic apparatus for measurement, and the absorption coefficient and positions of the mimic tumors are measured with the diagnostic apparatus. The apparatus is thus calibrated with reference to the measurements.

EXAMPLES

The present invention will be further described with reference to Examples, but it is not limited to the following Examples. For Examples and Comparative Examples, the number-average molecular weights and active hydroxy group equivalent weights of polyether polyols, the active isocyanate group equivalent weights of isocyanates, and the densities, acoustic attenuation coefficients and Asker C hardnesses of urethane gels were measured as below.

(1) Number-Average Molecular Weight (Mn) and Weight-Average Molecular Weight (Mw)

Measurement was performed at 40° C. with a gel permeation chromatography (GPC) apparatus manufactured by WATERS through three columns connected in series: two Shodex KD-806M and a Shodex KD-802 column (each manufactured by Showa Denko), using N,N'-dimethylformamide as an eluent, and an refractive index (RI) detector. The measured number-average molecular weight and weight-average molecular weight were values in terms of polyethylene glycol.

(2) Active Hydroxy Group Equivalent Weight of Polyether Polyol

Each polyether polyol was dissolved in pyridine containing acetic anhydride, and the hydroxy groups were thus acetylated. Then, the excess of the acetylating agent was hydrolyzed into acetic acid with water. The acetic acid was titrated with potassium hydroxide. An inflection point on the titration curve is defined as the end point. The hydroxy value of the polyether polyol is calculated from the amount of the potassium hydroxide solution used to reach the end point. The active hydroxy group equivalent weight was derived from the hydroxyl value using the equation: hydroxy group equivalent weight (grams of 1 mol of hydroxy group)=molecular weight of potassium hydroxide (milligrams of 1 mol of potassium hydroxide, 56100 mg)/hydroxy value (mg KOH/g).

(3) Active Isocyanate Group Equivalent Weight of Isocyanate

An isocyanate was dissolved in a dehydrated toluene, and an excessive amount of di-n-butylamine solution was added to the solution of the isocyanate for a reaction. The unreacted di-n-butylamine was titrated with hydrochloric acid, and the inflection point on the titration curve was defined as the end point. The isocyanate group content was calculated from the amount of the hydrochloric acid used to reach the end point. The active isocyanate group equivalent weight was derived from the isocyanate group content using the equation: isocyanate group equivalent weight (grams of 1 mol of isocyanate group)=molecular weight of isocyanate (grams of 1 mol of isocyanate, 42 g)/(isocyanate group content/100). In the Examples and Comparative Examples, a hexamethylene diisocyanate trimer is used as the isocyanate. This isocyanate contains 21.7% of isocyanate groups; hence, the equivalent weight of the isocyanate groups was 194 g/mol.

(4) Density

The density of the urethane gel was measured in accordance with JIS K7112 (Plastics—Methods of determining the density and relative density of non-cellular plastics) with an electronic densimeter (MD-300S, manufactured by Alfa Mirage).

(5) Acoustic Attenuation Coefficient

The probe used for measuring acoustic attenuation coefficient included an ultrasonic transducer (transmitter) V303 (center frequency: 1 MHz) produced by Olympus NDT Inc. and a needle hydrophone (receiver) manufactured by Toray Engineering.

The transducer and the hydrophone were fixed within a water tank with a fixture in a state where the centers of the sound axes thereof coincide with each other. The distance between the transducer and the hydrophone was set at 40 mm.

For preparation of specimens, each mixture of polyether polyol preparation and isocyanate was poured into a mold of 100 mm by 100 mm with a thickness of 10 mm and was heated to be cured at 90° C. for one hour. Then, the cured resin was released from the mold to yield a specimen in a sheet form with dimensions of 100 mm by 100 mm and a thickness of 10 mm. The specimen was fixed with a fixture between the transducer and the hydrophone in such a manner that the incident angle of ultrasonic signals would be 0° with respect to the sheet of the specimen.

Next, 8-cycle sign waves (transmission voltage: 100 V) were transmitted from the transducer using a function generator WF1946 manufactured by NF Corporation. Then, the maximum amplitude of the voltage signal received by the hydrophone was measured when a specimen was set and when the specimen was not set, using an oscilloscope Wave Runner 64Xi manufactured by Teledyne LeCroy. The acoustic attenuation coefficient was derived from the maximum amplitudes when the specimen was set to the measurement system and when it is not set, using the following equation (3):

[Math. 4]

$$\alpha = -\frac{20}{t}\text{Log}\left(\frac{(Z_1+Z_2)^2}{4Z_1Z_2} \cdot \frac{A'}{A_0}\right) \quad (3)$$

where $\alpha$: attenuation coefficient (dB/cm/MHz)
t: thickness of specimen (cm)
A': maximum amplitude (mV) of received voltage signal when a specimen was set
$A_0$: maximum amplitude (mV) of received voltage signal when a specimen was not set
$Z_1$: acoustic impedance (megarayls) of water
$Z_2$: acoustic impedance (megarayls) of the specimen The acoustic impedance calculated using the equation (3) is a product of density and sound velocity. The sound velocity and density used in the calculation were actually measured. For determining sound velocity, the difference in arrival time of received waves was measured between the cases where a specimen was set and was not set in the same measurement system as in the measurement for acoustic attenuation coefficient by obtaining the cross correlation of waves observed in the oscilloscope. A sound velocity was thus derived from the difference in arrival time, using the following equation (4):

[Math. 5]

$$c_2 = \frac{t}{\tau + \frac{t}{c_1}} \quad (4)$$

where $C_1$: sound velocity (m/s) in water at the temperature of water during measurement
$C_2$: sound velocity (m/s) through specimen
t: thickness (cm) of the specimen
$\tau$: delay time (s) of received wave arrival when the specimen was set (6) Hardness An Asker rubber hardness meter Model C (Kobunshi Keiki Co., Ltd.) was pressed on each 10 mm thick urethane gel sample for measuring the hardness of the urethane gel.

This measurement was performed in accordance Appendix 2 "Type C test method of spring hardness" of JIS K7312-1996 (Physical testing methods for molded products of thermosetting polyurethane elastomers).

Preparation of Urethane Gel

Additives (urethanation catalyst, optical property-adjusting agent, plasticizer, etc.) were appropriately added to a polyether polyol, and the materials were sufficiently stirred to yield a polyether polyol preparation. After defoaming the preparation, an appropriate amount of an isocyanate was added to the preparation, and the materials were uniformly mixed without trapping air bubbles. The resulting mixture was poured into a mold. Then, the mixture in the mold was placed in an oven that had been heated to 90° C. in advance and heated at that temperature for 2 hours to yield a urethane gel. The resulting urethane gel was poured into a 100 mm by 100 mm by 10 mm in thickness to form a urethane gel specimen for measuring the acoustic properties and hardness. In addition, another specimen of about 10 g in weight was formed for density measurement.

Example 1

To 100 g of polytetramethylene glycol (number average molecular weight: 2000, hydroxy group equivalent weight: 988 g/mol) as a polyether polyol, 0.002 g of a urethanation catalyst (dibutyltin dilaurate, DBTDL) was added, and the mixture was sufficiently stirred to yield a polyether polyol preparation. Then, 19.6 g of an isocyanate (hexamethylene diisocyanate trimer, isocyanate group equivalent weight: 194 g/mol) was added to the preparation. After being uniformly mixed, the mixture was poured into a mold and heated at 90° C. for 2 hours to yield a urethane gel. The cross-linking index (CI) of the resulting urethane gel was 1951. For the physical properties of the urethane gel, the density was 1.03 g/cm$^3$; the sound velocity, 1520 m/s; the acoustic attenuation coefficient, 0.9 dB/cm/MHz; and the Asker C hardness, 77. These results suggest that the urethane gel is suitable for use as a phantom that is a mimic living body.

Example 2

To 100 g of polytetramethylene glycol (number average molecular weight: 2000, hydroxy group equivalent weight: 988 g/mol) as a polyether polyol were added 0.003 g of a urethanation catalyst (dibutyltin dilaurate, DBTDL), 25 g of a plasticizer (diisononyl phthalate), 0.0002 g of carbon black powder, and 0.17 g of titanium oxide powder. The mixture was sufficiently stirred to yield a polyether polyol preparation. Then, 19.6 g of an isocyanate (hexamethylene diisocyanate trimer, isocyanate group equivalent weight: 194 g/mol) was added to the preparation. After being uniformly mixed, the mixture was poured into a mold and heated at 90° C. for 2 hours to yield a urethane gel. The cross-linking index (CI) of the resulting urethane gel was 1951. For the physical properties of the urethane gel, the density was 1.02 g/cm$^3$; the sound velocity, 1495 m/s; the acoustic attenuation coefficient, 0.7 dB/cm/MHz; and the Asker C hardness, 77. These results suggest that the urethane gel is suitable for a phantom that is a mimic living body.

The transmittance and reflectance of an absorption coefficient measuring cell appropriately adjusted were measured with a spectrophotometer V-670 (manufactured by JASCO Corporation). The urethane gel was cured into another sample of 10 mm by 10 mm by 50 mm, and the refractive index of the sample was measured with a refractometer KPR-2000 (manufactured by Shimadzu Corporation). Using these measurement results, variables were optimized so as to minimize the differences between the measured values and calculation results by Monte Carlo simulation, and thus the absorption coefficient and scattering coefficient at some wavelengths were calculated. At a wavelength of 756 nm in the near infrared region, the absorption coefficient was 0.01 mm$^{-1}$ and the scattering coefficient was 1.0 mm$^{-1}$. Thus the sample exhibited optical properties similar to a living body (human mammary gland tissue). These results suggest that the urethane gel is suitable for use as a phantom having optical properties simulating the living body, in terms of both acoustic properties and optical properties.

Example 3

To 100 g of a copolymer of ethylene glycol and propylene glycol (number average molecular weight: 3000, hydroxy group equivalent weight: 1476 g/mol) as a polyether polyol, 0.012 g of a urethanation catalyst (dibutyltin dilaurate, DBTDL) was added, and the mixture was sufficiently stirred to yield a polyether polyol preparation. Then, 13.1 g of an isocyanate (hexamethylene diisocyanate trimer, isocyanate group equivalent weight: 194 g/mol) was added to the preparation. After being uniformly mixed, the mixture was poured into a mold and heated at 90° C. for 2 hours to yield a urethane gel. The cross-linking index (CI) of the resulting urethane gel was 2907. For the physical properties of the urethane gel, the density was 1.09 g/cm$^3$; the sound velocity, 1526 m/s; the acoustic attenuation coefficient, 0.9 dB/cm/MHz; and the Asker C hardness, 45. These results suggest that the urethane gel is suitable for use as a phantom that is a mimic living body.

Example 4

To 100 g of a copolymer of ethylene glycol and propylene glycol (number average molecular weight: 3000, hydroxy group equivalent weight: 1002 g/mol) as a polyether polyol, 0.012 g of a urethanation catalyst (dibutyltin dilaurate, DBTDL) was added, and the mixture was sufficiently stirred to yield a polyether polyol preparation. Then, 15.5 g of an isocyanate (hexamethylene diisocyanate trimer, isocyanate group equivalent weight: 194 g/mol) was added to the preparation. After being uniformly mixed, the mixture was poured into a mold and heated at 90° C. for 2 hours to yield a urethane gel. The cross-linking index (CI) of the resulting urethane gel was 1880. For the physical properties of the urethane gel, the density was 1.06 g/cm$^3$; the sound velocity, 1425 m/s; the acoustic attenuation coefficient, 1.3 dB/cm/MHz; and the Asker C hardness, 71. These results suggest that the urethane gel is suitable for use as a phantom that is a mimic living body.

Example 5

To 100 g of a copolymer of ethylene glycol and propylene glycol (number average molecular weight: 3000, hydroxy group equivalent weight: 1476 g/mol) as a polyether polyol, 0.011 g of a urethanation catalyst (dibutyltin dilaurate, DBTDL) was added, and the mixture was sufficiently stirred to yield a polyether polyol preparation. Then, 9.8 g of an isocyanate (hexamethylene diisocyanate trimer, isocyanate group equivalent weight: 194 g/mol) was added to the preparation. After being uniformly mixed, the mixture was poured into a mold and heated at 90° C. for 2 hours to yield a urethane gel. The cross-linking index (CI) of the resulting urethane gel was 3876. For the physical properties of the urethane gel, the density was 1.10 g/cm$^3$; the sound velocity, 1523 m/s; the acoustic attenuation coefficient, 0.7 dB/cm/MHz; and the Asker C hardness, 34. These results suggest that the urethane gel is suitable for use as a phantom that is a mimic living body.

Example 6

To 100 g of a copolymer of ethylene glycol and propylene glycol (number average molecular weight: 5000, hydroxy group equivalent weight: 2527 g/mol) as a polyether polyol, 0.011 g of a urethanation catalyst (dibutyltin dilaurate, DBTDL) was added, and the mixture was sufficiently stirred to yield a polyether polyol preparation. Then, 8.4 g of an isocyanate (hexamethylene diisocyanate trimer, isocyanate group equivalent weight: 194 g/mol) was added to the preparation. After being uniformly mixed, the mixture was poured into a mold and heated at 90° C. for 2 hours to yield a urethane gel. The cross-linking index (CI) of the resulting urethane gel was 4645. For the physical properties of the urethane gel, the density was 1.09 g/cm$^3$; the sound velocity, 1508 m/s; the acoustic attenuation coefficient, 0.8 dB/cm/MHz; and the Asker C hardness, 32. These results suggest that the urethane gel is suitable for use as a phantom that is a mimic living body.

Comparative Example 1

To 100 g of a copolymer of ethylene glycol and propylene glycol (number average molecular weight: 7000, hydroxy group equivalent weight: 3117 g/mol) as a polyether polyol, 0.002 g of a urethanation catalyst (dibutyltin dilaurate, DBTDL) and 85 g of a plasticizer (diisononyl phthalate) were added, and the mixture was sufficiently stirred to yield a polyether polyol preparation. Then, 5.7 g of an isocyanate (hexamethylene diisocyanate trimer, isocyanate group equivalent weight: 194 g/mol) was added to the preparation. After being uniformly mixed, the mixture was poured into a mold and heated at 90° C. for 2 hours to yield a urethane gel. The cross-linking index (CI) of the resulting urethane gel was 1880. For the physical properties of the urethane gel, the density was 1.01 g/cm³; the sound velocity, 1400 m/s; the acoustic attenuation coefficient, 0.5 dB/cm/MHz; and the Asker C hardness, 13. The hardness of the urethane gel was insufficient for use as a phantom.

Comparative Example 2

To 100 g of a copolymer of ethylene glycol and propylene glycol (number average molecular weight: 3000, hydroxy group equivalent weight: 1476 g/mol) as a polyether polyol, 0.005 g of a urethanation catalyst (dibutyltin dilaurate, DBTDL) was added, and the mixture was sufficiently stirred to yield a polyether polyol preparation. Then, 6.6 g of an isocyanate (hexamethylene diisocyanate trimer, isocyanate group equivalent weight: 194 g/mol) was added to the preparation. After being uniformly mixed, the mixture was poured into a mold and heated at 90° C. for 2 hours. The sample was however too viscous to measure the physical properties. The cross-linking index (CI) of the urethane gel was 5813.

Comparative Example 3

To 100 g of a copolymer of ethylene glycol and propylene glycol (number average molecular weight: 5000, hydroxy group equivalent weight: 2527 g/mol) as a polyether polyol, 0.005 g of a urethanation catalyst (dibutyltin dilaurate, DBTDL) was added, and the mixture was sufficiently stirred to yield a polyether polyol preparation. Then, 5.7 g of an isocyanate (hexamethylene diisocyanate trimer, isocyanate group equivalent weight: 194 g/mol) was added to the preparation. After being uniformly mixed, the mixture was poured into a mold and heated at 90° C. for 2 hours. The sample was however too viscous to measure the physical properties. The cross-linking index (CI) of the urethane gel was 6812.

Comparative Example 4

To 100 g of polytetramethylene glycol (number average molecular weight: 650, hydroxy group equivalent weight: 326 g/mol) as a polyether polyol, 0.008 g of a urethanation catalyst (dibutyltin dilaurate, DBTDL) was added, and the mixture was sufficiently stirred to yield a polyether polyol preparation. Then, 18.6 g of an isocyanate (hexamethylene diisocyanate trimer, isocyanate group equivalent weight: 194 g/mol) was added to the preparation. After being uniformly mixed, the mixture was poured into a mold and heated at 90° C. for 2 hours to yield a urethane gel. The cross-linking index (CI) of the resulting urethane gel was 654. For the physical properties of the urethane gel, the density was 1.08 g/cm³; the sound velocity, 1614 m/s; the acoustic attenuation coefficient, 7.4 dB/cm/MHz; and the Asker C hardness, 92. The urethane gel was unsuitable for use as a phantom that is a mimic living body because of the high acoustic attenuation coefficient.

Comparative Example 5

To 100 g of polytetramethylene glycol (number average molecular weight: 650, hydroxy group equivalent weight: 326 g/mol) as a polyether polyol, 0.011 g of a urethanation catalyst (dibutyltin dilaurate, DBTDL) and 58 g of a plasticizer (diisononyl phthalate) were added, and the mixture was sufficiently stirred to yield a polyether polyol preparation. Then, 59.4 g of an isocyanate (hexamethylene diisocyanate trimer, isocyanate group equivalent weight: 194 g/mol) was added to the preparation. After being uniformly mixed, the mixture was poured into a mold and heated at 90° C. for 2 hours to yield a urethane gel. The cross-linking index (CI) of the resulting urethane gel was 654. For the physical properties of the urethane gel, the density was 1.08 g/cm³; the sound velocity, 1546 m/s; the acoustic attenuation coefficient, 3.7 dB/cm/MHz; and the Asker C hardness, 79. The urethane gel was unsuitable for use as a phantom that is a mimic living body because of the high acoustic attenuation coefficient.

Comparative Example 6

To 100 g of a copolymer of ethylene glycol and propylene glycol (number average molecular weight: 1000, hydroxy group equivalent weight: 510 g/mol) as a polyether polyol, 0.003 g of a urethanation catalyst (dibutyltin dilaurate, DBTDL) was added, and the mixture was sufficiently stirred to yield a polyether polyol preparation. Then, 13.8 g of an isocyanate (hexamethylene diisocyanate trimer, isocyanate group equivalent weight: 194 g/mol) was added to the preparation. After being uniformly mixed, the mixture was poured into a mold and heated at 90° C. for 2 hours to yield a urethane gel. The cross-linking index (CI) of the resulting urethane gel was 1041. For the physical properties of the urethane gel, the density was 1.06 g/cm³; the sound velocity, 1551 m/s; the acoustic attenuation coefficient, 2.5 dB/cm/MHz; and the Asker C hardness, 87. The urethane gel was unsuitable for use as a phantom that is a mimic living body because of the high acoustic attenuation coefficient.

Comparative Example 7

To 100 g of polytetramethylene glycol (number average molecular weight: 3000, hydroxy group equivalent weight: 1002 g/mol) as a polyether polyol, 0.006 g of a urethanation catalyst (dibutyltin dilaurate, DBTDL) was added, and the mixture was sufficiently stirred to yield a polyether polyol preparation. Then, 19.3 g of an isocyanate (hexamethylene diisocyanate trimer, isocyanate group equivalent weight: 194 g/mol) was added to the preparation. After being uniformly mixed, the mixture was poured into a mold and heated at 90° C. for 2 hours to yield a urethane gel. The cross-linking index (CI) of the resulting urethane gel was 1504. For the physical properties of the urethane gel, the density was 1.06 g/cm³; the sound velocity, 1442 m/s; the acoustic attenuation coefficient, 2.8 dB/cm/MHz; and the Asker C hardness, 73. The urethane gel was unsuitable for use as a phantom that is a mimic living body because of the high acoustic attenuation coefficient.

Comparative Example 8

To 100 g of a copolymer of hexanediol and pentanediol (number average molecular weight: 2000, hydroxy group equivalent weight: 1004 g/mol) as a polycarbonate polyol, 0.006 g of a urethanation catalyst (dibutyltin dilaurate, DBTDL) was added, and the mixture was sufficiently stirred to yield a polycarbonate polyol preparation. Then, 14.5 g of an isocyanate (hexamethylene diisocyanate trimer, isocyanate group equivalent weight: 194 g/mol) was added to the preparation. After being uniformly mixed, the mixture was poured into a mold and heated at 90° C. for 2 hours to yield a urethane gel. The cross-linking index (CI) of the resulting urethane gel was 2686. For the physical properties of the urethane gel, the density was 1.12 g/cm³; the sound velocity, 1557 m/s; the acoustic attenuation coefficient, 3.5 dB/cm/MHz; and Asker C hardness, 72. The urethane gel was unsuitable for use as a phantom that is a mimic living body because of the high acoustic attenuation coefficient.

The results are shown in Tables 1 and 2.

TABLE 1

|  | Example 1 | Example 2 | Example 3 | Example 4 | Example 5 | Example 6 |
| --- | --- | --- | --- | --- | --- | --- |
| Cross-linking index | 1951 | 1951 | 2907 | 1880 | 3876 | 4645 |
| Sound velocity (m/s) | 1520 | 1495 | 1526 | 1425 | 1523 | 1508 |
| Acoustic attenuation coefficient (dB/cm/MHz) | 0.9 | 0.7 | 0.9 | 1.3 | 0.7 | 0.8 |
| Density | 1.03 | 1.01 | 1.09 | 1.06 | 1.10 | 1.09 |
| Acoustic impedance | 1.57 | 1.51 | 1.67 | 1.51 | 1.67 | 1.65 |
| Hardness (Asker C) | 77 | 69 | 45 | 71 | 34 | 32 |

TABLE 2

|  | Comparative Example 1 | Comparative Example 2 | Comparative Example 3 | Comparative Example 4 | Comparative Example 5 | Comparative Example 6 | Comparative Example 7 | Comparative Example 8 |
| --- | --- | --- | --- | --- | --- | --- | --- | --- |
| Cross-linking index | 5734 | 5813 | 6812 | 654 | 654 | 1041 | 1504 | 2686 |
| Sound velocity (m/s) | 1400 | — | — | 1614 | 1546 | 1551 | 1442 | 1557 |
| Acoustic attenuation coefficient (dB/cm/MHz) | 0.5 | — | — | 7.4 | 3.7 | 2.5 | 2.8 | 3.5 |
| Density | 1.01 | — | — | 1.08 | 1.08 | 1.05 | 1.06 | 1.12 |
| Acoustic impedance | 1.41 | — | — | 1.74 | 1.66 | 1.64 | 1.53 | 1.74 |
| Hardness (Asker C) | 13 | Unmeasurable (liquid) | Unmeasurable (liquid) | 92 | 79 | 87 | 73 | 72 |

FIGS. 1 and 2 show the above results together.

FIG. 1 is a plot of the relationship between the cross-linking index and the acoustic attenuation coefficient. The lines in FIG. 1 are each an approximated curve for the results of the Examples or Comparative Examples in which the urethane gel did not contain a plasticizer so as to cancel the influences of the plasticizer on the acoustic attenuation coefficient. The intersection of the two line lies at a cross-linking index of about 1650.

It was found, as shown in FIG. 1, that the urethanes gels made of a polyether polyol and an isocyanate and having cross-linking indices in the range of 1600 or more exhibited increase in acoustic attenuation coefficient as the cross-linking index is reduced.

It was also fund that polycarbonate polyols, whose intermolecular aggregation power is high, exhibit stronger intermolecular interaction than polyether polyols and high acoustic attenuation coefficient, and are therefore unsuitable for use as diagnostic phantoms.

FIG. 2 is a plot of the relationship between the cross-linking index and the hardness (Asker C). The line in FIG. 2 is the linear approximated curve and shows that the hardness comes to 20 at a cross-linking index of about 5000. If the hardness is less than 20, the urethane gel becomes too soft to use as the phantom of an embodiment of the present invention. In the case of a hardness of 20 or more, however, the phantom was not deformed much, exhibiting the intended effect of the embodiment.

The results of the Examples and Comparative Examples suggest that the urethane gel according to an embodiment of the invention can be suitable for use as ultrasonic and acoustic phantoms. The present invention provides a phantom that exhibits acoustic attenuation similar to the human body and can accurately keep the position of the target or signal source therein.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-247129, filed Nov. 29, 2013, which is hereby incorporated by reference herein in its entirety.

The invention claimed is:

1. An acoustic phantom comprising a urethane gel produced by a reaction of a polyether polyol and an isocyanate, the urethane gel having a cross-linking index in the range of 1600 to 5000, the cross-linking index being defined by the following equation (1):

[Math. 1]

$$CI = \frac{W_{OH}/C_{OH}}{([NCO]/[OH]) \cdot [([OH]/C_{OH}) - 1]} \quad (1)$$

$$C_{OH} = W_{OH}/M_{OH}$$
$$[OH] = W_{OH}/Eq_{OH}$$
$$[NCO] = W_0/Eq_0$$

wherein $W_U$ represents the total weight of the urethane gel;

$W_0$ represents the weight of the isocyanate in $W_U$ of the urethane gel;

$W_{OH}$ represents the weight of the polyether polyol in $W_U$ of the urethane gel;

$M_{OH}$ represents the number-average molecular weight of the polyether polyol;

$Eq_{OH}$ represents the active hydroxy group equivalent weight of the polyether polyol;

$Eq_0$ represents the active isocyanate group equivalent weight of the isocyanate;

$C_{OH}$ represents the total moles of the polyether polyol in $W_U$ of the urethane gel;

[OH] represents the moles of the active hydroxy group in $W_U$ of the urethane gel; and

[NCO] represents the moles of the active isocyanate group in $W_U$ (g) of the urethane gel.

2. The acoustic phantom according to claim 1, wherein the polyether polyol comprises a copolymer of ethylene glycol and propylene glycol.

3. The acoustic phantom according to claim 1, wherein the isocyanate contains hexamethylene diisocyanate trimer.

4. The acoustic phantom according to claim 1, wherein the urethane gel contains an optical property-adjusting agent.

5. The acoustic phantom according to claim 4, wherein the optical property-adjusting agent contains at least one of carbon black and phthalocyanine compounds.

6. The acoustic phantom according to claim 4, wherein the optical property-adjusting agent is titanium oxide.

* * * * *